United States Patent
Hempel et al.

(10) Patent No.: US 7,561,658 B2
(45) Date of Patent: Jul. 14, 2009

(54) METHOD AND X-RAY COMPUTED TOMOGRAPHY SYSTEM FOR VISUALIZING AT LEAST TWO TYPES OF CARDIAC TISSUE: HEALTHY TISSUE AND DISEASED TISSUE

(75) Inventors: Eckhard Hempel, Fürth (DE); Martin Hoheisel, Erlangen (DE); Stefan Popescu, Erlangen (DE); Rainer Raupach, Heroldsbach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/222,349

(22) Filed: Aug. 7, 2008

(65) Prior Publication Data

US 2009/0052611 A1 Feb. 26, 2009

(30) Foreign Application Priority Data

Aug. 8, 2007 (DE) ............. 10 2007 037 380

(51) Int. Cl.
*A61B 6/00* (2006.01)
(52) U.S. Cl. .................. 378/4; 378/8; 378/19
(58) Field of Classification Search ............ 378/4, 378/5, 8, 15, 16, 18, 19, 20; 382/128, 131, 382/132
See application file for complete search history.

(56) References Cited

U.S. PATENT DOCUMENTS

| | | | |
|---|---|---|---|
| 6,865,248 B1 * | 3/2005 | Rasche et al. | 378/8 |
| 7,006,593 B2 * | 2/2006 | Kokubun et al. | 378/8 |
| 7,415,093 B2 * | 8/2008 | Tkaczyk et al. | 378/8 |
| 2004/0017881 A1 * | 1/2004 | Cesmeli et al. | 378/4 |
| 2006/0173297 A1 | 8/2006 | Popescu | |
| 2008/0056547 A1 * | 3/2008 | Kokubun et al. | 382/128 |

FOREIGN PATENT DOCUMENTS

DE 10 2004 055 461 5/2006

OTHER PUBLICATIONS

Stampanoni M. et al., "Phase Contraast Imaging: A New Tool for Biomedical Investigations" in IEEE International Symposium on Biomedical Imaging: Macro to Nano, Apr. 6-9, 2006, pp. 1100-1103; Others.
German Office Action dated Feb. 28, 2008.

* cited by examiner

*Primary Examiner*—Irakli Kiknadze
(74) *Attorney, Agent, or Firm*—Harness Dickey & Pierce

(57) ABSTRACT

A method and an x-ray computed tomography system are disclosed for visualizing at least two different types of cardiac tissue, such as normally perfused tissue, hypoperfused tissue and scarred tissue. In at least one embodiment, this is done by use of an imaging tomographic recording technique with the aid of x-ray radiation, wherein at least one cardiac region of a patient is scanned by x-ray radiation which passes through a first grating for the passing-through x-ray radiation, designed as an absorption grating, prior to reaching the patient, and at least the locally caused phase-shifts of the x-ray radiation in the cardiac region are also made detectable by using a second grating for the passing-through x-ray radiation, designed as a phase grating, downstream of the patient in the emission direction, and the spatial distribution of these shifts is measured and reconstructed, wherein an average specific phase-shift value is assigned to each spatial unit, wherein each of the abovementioned tissue types are assigned to a region of a typical specific phase-shift value and at least one region assigned to a tissue type is optically highlighted in a view of the cardiac region.

21 Claims, 3 Drawing Sheets

US 7,561,658 B2

METHOD AND X-RAY COMPUTED TOMOGRAPHY SYSTEM FOR VISUALIZING AT LEAST TWO TYPES OF CARDIAC TISSUE: HEALTHY TISSUE AND DISEASED TISSUE

PRIORITY STATEMENT

The present application hereby claims priority under 35 U.S.C. §119 on German patent application number DE 10 2007 037 380.7 filed Aug. 8, 2007, the entire contents of which is hereby incorporated herein by reference.

FIELD

Embodiments of the invention generally relate to a method for visualizing at least two tissue types. For example, at least one embodiment relates to a method for visualizing at least two tissue types: healthy tissue and diseased tissue of a heart by way of an imaging tomographic recording technique with the aid of x-ray radiation, wherein at least one cardiac region of a patient is scanned by x-ray radiation which passes through a first x-ray absorption grating prior to reaching the patient, and at least the locally caused phase-shifts of the x-ray radiation in the cardiac region are also made detectable by using a second phase grating downstream of the patient in the emission direction, and the spatial distribution of these shifts is measured and reconstructed, wherein an average specific phase-shift value ($\Delta\phi/s[°/mm]$) is assigned to each spatial unit (=voxel or pixel).

Embodiments of the invention additionally generally relate to an x-ray computed tomography system. For example, at least one embodiment relates to an x-ray computed tomography system including at least one scanning system rotating about a system axis comprising a radiation source, an x-ray absorption grating, a phase grating and a detector to determine the absorption and/or the phase-contrast, wherein a patient can be in the region between the x-ray absorption grating and the phase-contrast grating, and furthermore comprising a control and computational unit which has a memory with computer programs to control the x-ray computed tomography system and to reconstruct tomographic views.

BACKGROUND

Imaging techniques for visualizing coronary heart diseases, in particular for visualizing coronary calcification or stenoses, constitute an important aid in evaluating the condition of the heart. This relates to both preliminary examinations for early diagnosis of circulatory disorders and monitoring a coronary heart disease over a longer period, after a bypass operation or an angioplasty if necessary. Such examinations can improve estimates regarding the risk of a heart attack and can review the success of an intervention or therapy. In particular, non-invasive imaging techniques such as computed tomography (CT), magnetic resonance imaging (MRI) or positron emission tomography (PET) are preferably used these days. However, the measurement of cardiac perfusion using PET is very costly and only supplies limited spatial resolution.

Images of the cardiac vessel tree in which vascular restrictions are recognizable can be recorded using coronary CT angiography (CTA) after a contrast agent has been injected. However, even this technique's spatial resolution is still limited due to movement artifacts. Hence, it is no longer possible to make reliable statements about vascular restrictions from such images for volumes below 1 mm$^3$, which occur in the case of vascular restrictions in peripheral coronary artery segments RCA1-4, LM5, LAD6-9 or CX, for example, with lumen cross sections down to 1 mm.

The German patent application with reference number DE 10 2004 055 461.7 furthermore specifies a non-invasive imaging method and an apparatus for visualizing coronary heart diseases, the images of which also make it possible to recognize vascular restrictions or vascular occlusions which previously could not be verified using conventional CTA. The color-coded display of undersupplied or necrotic myocardial areas in a cardiac surface image is also described in this document.

In this case it is problematic that even when a contrast agent is present, the absorption of x-ray radiation in healthy and diseased soft tissue differs only very slightly—approximately 3-5 HU—and this results in large uncertainties when detecting changes in the tissue. Furthermore, these low differences in HU values also require relatively high doses during the examination in order to limit the dose-dependent noise. Although PET allows better differentiation between tissue types than absorption CT, the costs and the radiation exposure of the patient are significantly higher. Furthermore, the spatial resolution of PET examinations is relatively low compared to the resolutions possible in CT.

SUMMARY

In at least one embodiment of the invention, a method and/or an apparatus are defined which at least allow to distinguish between healthy and diseased soft tissue in the region of the heart and in which the spatial resolution should be improved compared to conventional PET examinations.

The inventors, in at least one embodiment, have recognized that differences in tissue conditions, which occur between healthy, normally perfused, functioning cardiac tissue and diseased, hypoperfused tissue or dead, scarred tissue, lead to effective changes in their influence on the phase-shift of x-ray radiation. As a result, it is also possible to detect these tissue differences in spatially highly-resolved conditions with the aid of x-ray phase-contrast computed tomography, with these tissue differences establishing a significantly larger bandwidth of measured value differences than the absorption measurement of x-ray radiation.

Furthermore, the recording technique is significantly faster than a PET examination, so cardiac motion can be "frozen" using a technique similar to that of the known triggered cardio-CT examination. By way of example, an ECG signal, mechanical pressure pulses, detected movements in the CT image itself or any other known technique can be used as a trigger signal.

This phase-contrast computed tomography technique records and reconstructs one or more images of the heart or of a cardiac region, ideally without administering a contrast agent. A local undersupply or perfusion disorder of the myocardium can be displayed using an x-ray phase-contrast examination.

In contrast to known CTA, in which one or more images of the cardiac vessel tree are recorded shortly after the injection of contrast agent when the maximum contrast agent flow occurs in the vessels of the vessel tree, at least one embodiment of the present method primarily records without using a contrast agent. The contrast resolution, improved by means of phase-contrast x-ray imaging, leads to a distinguishable measured value distribution between the vessel tree and myocardium, and also between areas within the myocardium having different levels of blood supply. Necrotic regions, which no longer have significant perfusion, and so-called lesions, which are undersupplied at the time of measurement to the extent that irreversible damage can be assumed to occur if no therapy is undertaken and necrosis spreading being a worst case scenario, generate a significantly different contrast than healthy and normally perfused regions.

The assignment of measured values to a particular functionality of the tissue can be written to a look-up table. By way of example, the display of myocardial regions of clinical interest, such as necroses, lesions and healthy tissue, can be color-coded or optically highlighted in any other manner on a cardiac surface image; this cardiac surface image can in particular be generated from x-ray absorption data.

In accordance with this basic idea, the inventors propose a method, in at least one embodiment, for visualizing at least two tissue types: healthy tissue and diseased tissue of a heart by way of an imaging tomographic recording technique with the aid of x-ray radiation, wherein at least one cardiac region of a patient is scanned by x-ray radiation which passes through a first x-ray absorption grating prior to reaching the patient, and at least the locally caused phase-shifts of the x-ray radiation in the cardiac region are also made detectable by using a second phase grating downstream of the patient in the emission direction, and the spatial distribution of these shifts is measured and reconstructed, wherein an average specific phase-shift value is assigned to each spatial unit, that is to say to each voxel or pixel. According to the invention, each of the abovementioned tissue types are now assigned to a region of a typical specific phase-shift value, and at least one region assigned to a tissue type is optically highlighted in a view of the cardiac region.

Hence, this method according to at least one embodiment of the invention distinguishes between healthy and diseased tissue and this is displayed optically in a noticeable manner for the observer. This results in a significantly higher resolution than a PET examination and makes it possible to localize the diseased places in a more precise manner and without any problems.

In an improved variant of the method according to at least one embodiment of the invention, the diseased tissue can be subdivided into tissue with a reversible disease, namely lesions, and tissue with an irreversible disease, namely necroses, with different associated phase-shift value regions, so that each region in turn can be specifically illustrated optically. This makes it possible to carry out a further improved differential diagnosis of the heart.

The inventors furthermore propose that the phase-shift value regions and their assignment to the individual tissue types are stored in a look-up table.

Absorption data can also be obtained in addition to the phase-contrast data, wherein it is possible that at least one 3D absorption data record is reconstructed from the absorption data, or it is possible that a 3D view of the heart is generated from the at least one 3D absorption data record.

In this regard, reference is made to the fact that by summing the measured values during the phase-contrast data measurement, it is also possible to obtain absorption values at the same time so that a new scan to calculate absorption values is not necessarily required. However, without departing from the scope of the invention, it is alternatively possible to carry out a pure absorption measurement in parallel by using a second emitter-detector combination which is designed to measure only absorption values.

If such a 3D absorption view is present, the phase-contrast data can be superposed onto it so that it is possible to correspondingly highlight diseased areas in an image region which is otherwise familiar to a medical practitioner.

In a particular embodiment of the proposed method, it is possible that cardiac phases of the scan of the patient are determined and that in each case measurement data of the same cardiac phases is processed together. This corresponds to the conventional procedure of other cardio-CT measurements, in which overall reconstructible data records are generated by collecting measurement data during identical cardiac phases so that a "freeze-image" can be generated for a particular cardiac phase. By way of example, the cardiac phases themselves can be measured by way of an ECG or by other direct or indirect detection of cardiac activity.

In accordance with a development of the method according to at least one embodiment of the invention, the inventors furthermore propose that at least the phase-contrast views are recorded using at least two temporally separated examinations, and that difference images, so-called phase-contrast difference images, of the temporally different phase-contrast views are generated. By generating these phase-contrast difference images it is possible to determine the progression of an illness or the progression of the treatment of an illness particularly well. By way of example, the success of bypass operations or a medicinal treatment can be determined particularly well, even over a longer period of time.

A 3D absorption data record can also be superposed onto such phase-contrast difference images to provide the observer with a conventional view.

When such examinations are undertaken at different times, it is often possible that a precise spatial match must be ensured to generate difference images. This can come about by generating absorption views parallel to the phase-contrast views and by registering the phase-contrast images to the contours of the absorption images prior to the creation of phase-contrast difference images.

Hence, a spatial normalization of the phase-contrast images is generated by this registration on the basis of the anatomical structures that can be recognized in the absorption views so that the phase-contrast difference images generated therefrom are not influenced by a spatial displacement of the examined heart.

Additionally, it is possible that at least one of the absorption views is generated after prior administration of an absorption contrast agent. This additionally allows displaying vessels particularly well in a known manner so that the observer also sees the conventional image in superposed cardiac views.

In accordance with at least one embodiment of the previously described method, the inventors also propose at least one embodiment of an x-ray computed tomography system comprising at least one scanning system rotating about a system axis comprising a radiation source, an x-ray absorption grating, a phase grating and a detector to determine the absorption and/or the phase-contrast, wherein a patient can be in the region between the x-ray absorption grating and the phase-contrast grating, with the x-ray computed tomography system furthermore comprising a control and computational unit which has a memory with computer programs to control the x-ray computed tomography system and to reconstruct tomographic views. According to at least one embodiment of the invention, this x-ray computed tomography system is also intended to comprise computer programs with program code in the memory of the control and computational unit which carry out at least one embodiment of the method described above during operation.

BRIEF DESCRIPTION OF THE DRAWINGS

In the following, the invention is described in more detail on the basis of example embodiments with the aid of the figures, with only features required to understand the invention being illustrated. In this context, the following reference symbols are used: 1: x-ray phase-contrast CT system; 2: first x-ray tube; 2.1: first grating of the first tube-detector system; 3: first detector; 3.1: second grating of the first tube-detector system; 4: second x-ray tube; 4.1: first grating of the second tube-detector system; 5: second detector; 5.1: second grating of the second tube-detector system; 6: gantry housing; 7: patient; 8: patient couch; 9: system axis; 10: control and computational unit; 11: memory of the control and computational unit; 12: region of healthy tissue; 13: region of diseased tissue; 13a: region of lesions; 13b: region of necroses; 14: heart; A, B, C: phase-contrast regions; I, Ia, Ib, II: states of the tissue; $Prg_1$-$Prg_x$: computer programs.

In detail.

DETAILED DESCRIPTION OF THE EXAMPLE EMBODIMENTS

Figure 1:
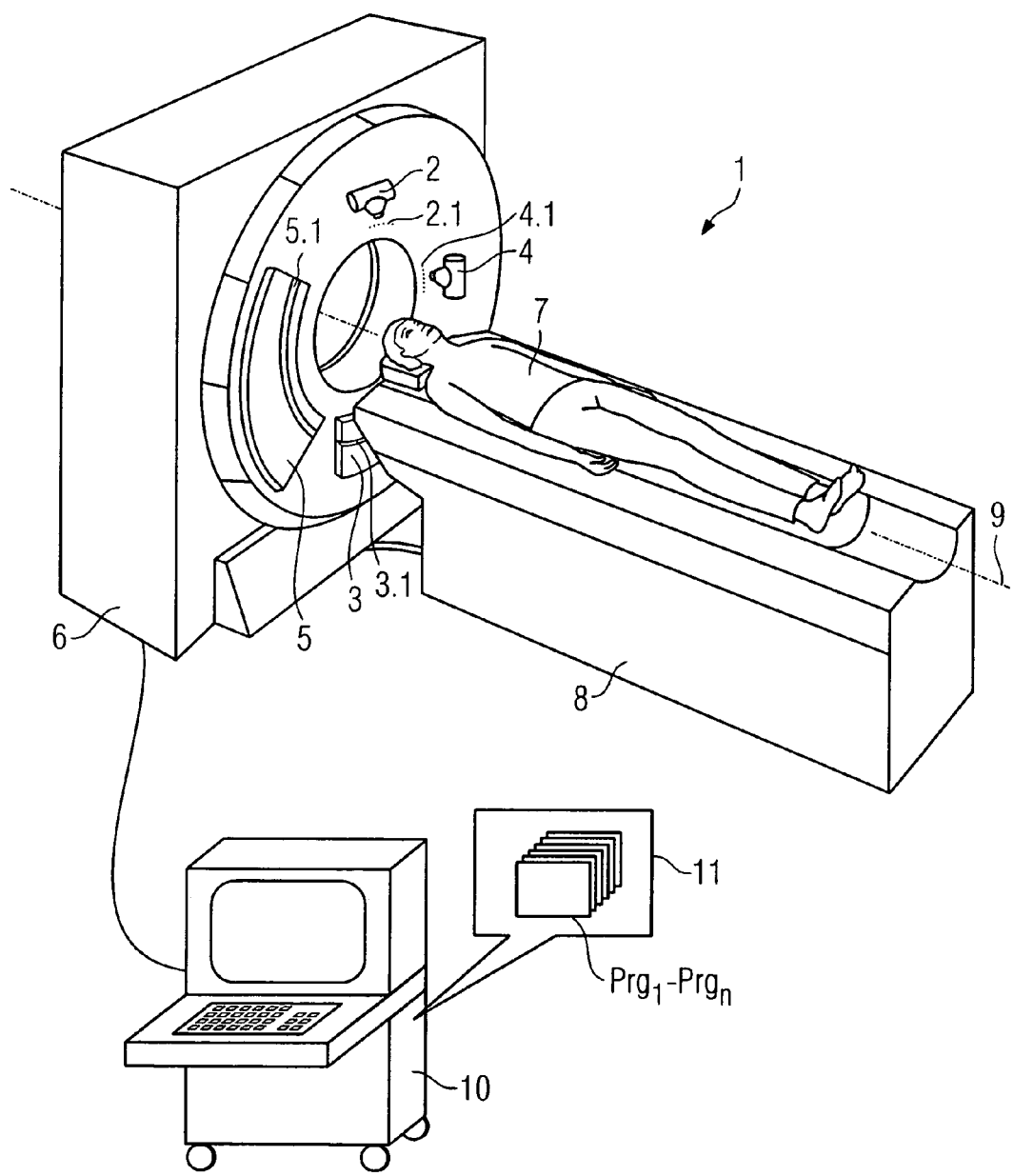
FIG. 1 shows an x-ray phase-contrast CT system for carrying out the method according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

By way of example, an x-ray phase-contrast CT system 1 as shown in FIG. 1 can be used to carry out the method according to an embodiment of the invention. This x-ray phase-contrast CT system 1 includes a gantry housing 6, with a rotatable gantry which lies inside and on which at least a first emitter-detector system and optionally further emitter-detector systems are arranged. In this case, the first emitter-detector system includes a first x-ray tube 2 with an x-ray absorption grating 2.1 which is arranged in front of the patient and is used to generate quasi-coherent x-ray radiation. Furthermore, the first emitter-detector system has a detector 3 arranged opposite to the x-ray tube 2 with an upstream x-ray grating 3.1 for generating interference and thus "making visible" the phase-shift of the x-ray radiation which differs depending on the observed beam passing through the patient 7. For scanning, the patient 7 on a patient couch 8 is pushed through the measurement field along the system axis 9, while the emitter-detector system on the gantry rotates about the system axis 9. However, it is possible to alternatively use a sequential scanning method, in which the patient 7 is pushed through the measurement field incrementally, with a circular scan being carried out during the intermediate times without feed.

The principle method of operation and particular embodiment of such phase-contrast CT systems has already been described explicitly a number of times in diverse previous applications from the applicant relating to phase-contrast CT, and in other publications in the prior art.

A further emitter-detector system, offset by 90°, is also shown in the illustrated CT system 1. This second emitter-detector system likewise comprises an x-ray tube 4 with an absorption grating 4.1 and a detector 5 with an upstream phase grating 5.1, and it co-rotates with the first emitter-detector system on the gantry about the system axis 9.

The CT system 1 is operated by a control and computational unit 10, with this control and computational unit 10 maintaining the work programs with their program code for operation in a main memory 11. Programs $Prg_1$ to $Prg_n$, inter alia, are also contained in this main memory which emulate the method according to an embodiment of the invention described above and which can execute it during operation.

Figure 2:
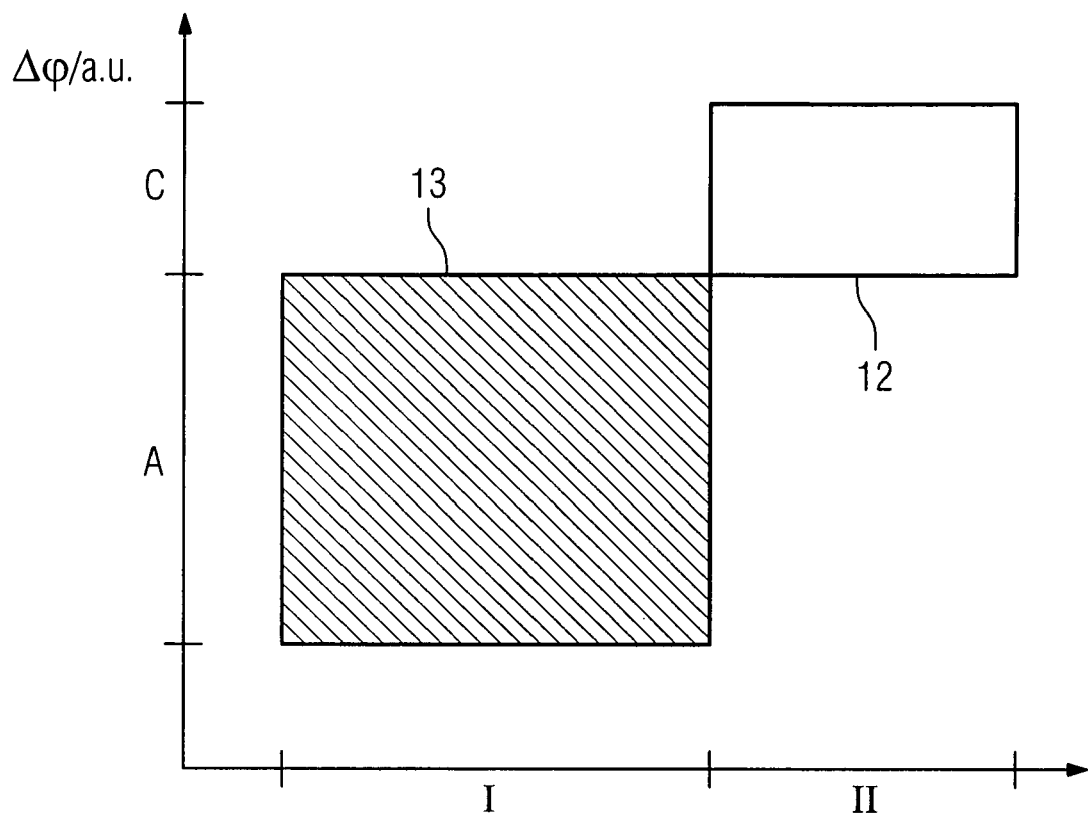
FIG. 2 shows a graphic illustration of a look-up table for two different tissue types.

FIG. 2 shows an example diagram of the correlation between specific phase-shift values $\Delta\phi$ in arbitrary units (a.u.) on the ordinate and the states of the tissue I=diseased tissue and II=healthy tissue on the abscissa. The region of healthy tissue is provided with reference symbol 12 and the region of diseased tissue is provided with reference symbol 13.

Figure 3:
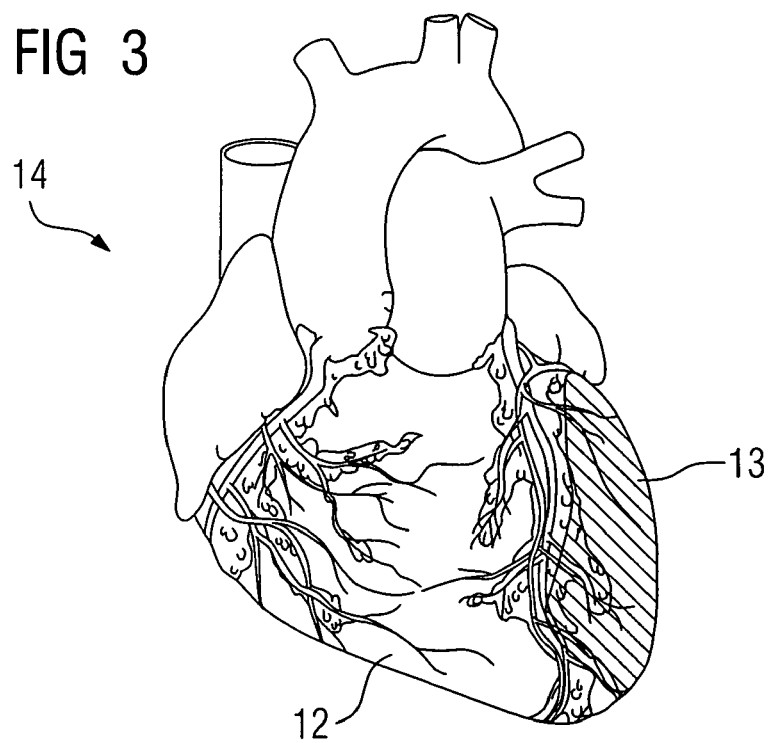
FIG. 3 shows an example view of the heart with optical highlighting of diseased regions.

By way of example, an illustration of a heart 14 as shown in FIG. 3 can be obtained if the specific phase-shift values are categorized into these two regions A and C. Here the heart 14 itself is shown with blood vessels in a three-dimensional surface view. Those areas in which a specific phase-contrast shift in region A of FIG. 2 was detected by the phase-contrast measurements are shaded 13 in the surface view of the heart 14, whereas healthy tissue 12 is not shaded. Of course, in place of this shading it is also possible to select a color illustration or a color highlighting scheme and, where appropriate, a differentiated color highlighting scheme in which the intensity or color frequency is correlated with the magnitude of the specific phase-shift.

Figure 4:
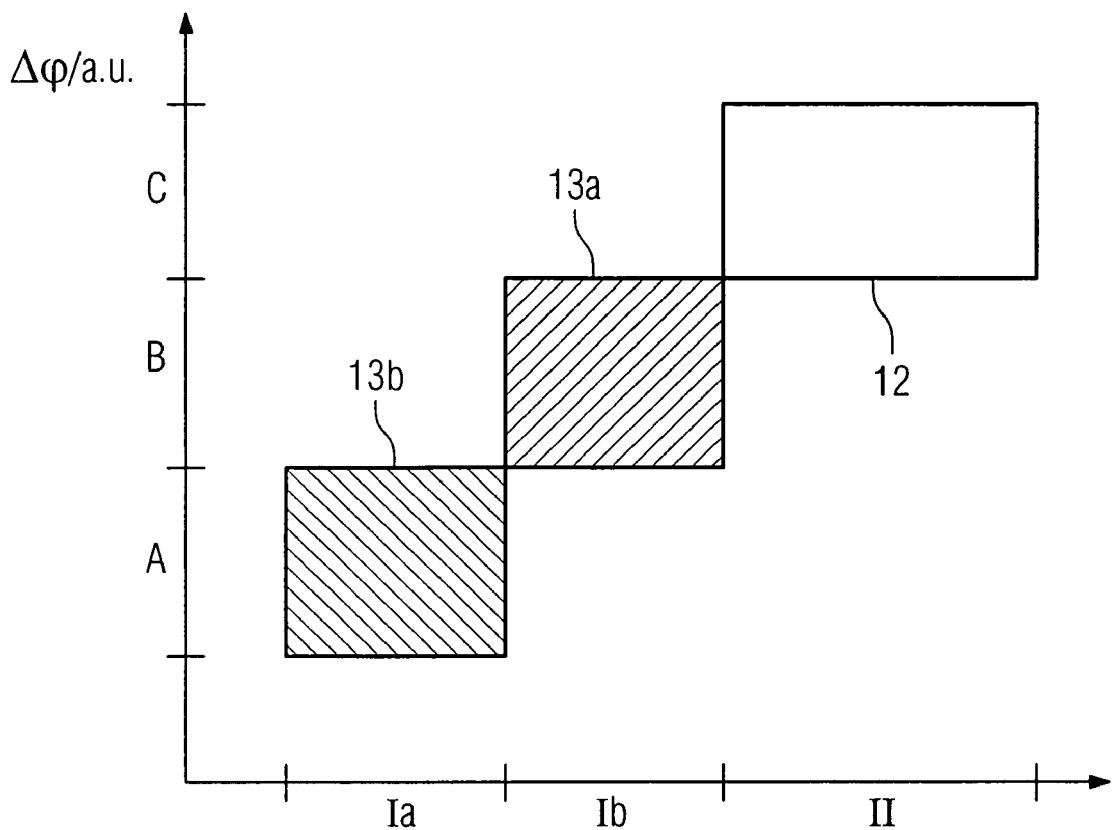
FIG. 4 shows a graphic illustration of a look-up table with three different regions of tissue.

If there is further differentiation in the categorizing of the diseased tissue, for example into necrosis corresponding to the region Ia and a lesion corresponding to the region Ib in FIG. 4 respectively, it is correspondingly possible to specify three value regions for the specific phase-shift value $\Delta\phi$; in this case A, B and C. The region 12 of healthy tissue is not shaded, the region of a reversible tissue lesion is provided with the reference symbol 13a and the region of tissue necrosis is provided with reference symbol 13b.

Figure 5:
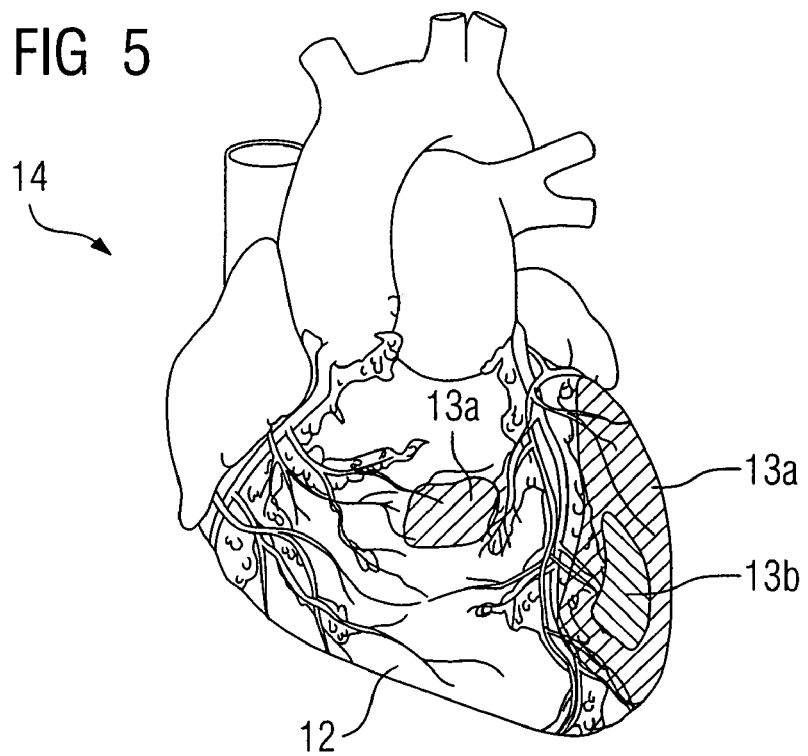
FIG. 5 shows an absorption view of a cardiac surface in 3D with optical highlighting of necrosis and two regions of lesions.

Superposing a cardiac view 14 from an absorption image with optical highlighting of these three individual areas then results in a view similar to that of FIG. 5. In this case, like in FIG. 4, healthy myocardial regions 12 are not shaded, whereas the regions of a lesion are superposed by shadings according to the field 13a and necrotic development in the myocardium is provided with reference symbol 13b, corresponding to a different shading.

Of course, this variant also allows the possibility of illustrating the highlighting in a more pronounced and differentiated manner by using a different color-code.

It is self-evident that the previously mentioned features of the invention can be used not only in the respectively specified combination, but rather it is the case that other combinations of the features, or the features on their own, can be used without departing from the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing at least two different types of cardiac tissue by way of an imaging tomographic recording technique with the aid of x-ray radiation, the method comprising:

scanning at least one cardiac region of a patient by x-ray radiation which passes through a first grating for the passing-through x-ray radiation, designed as an absorption grating, prior to reaching the patient;

detecting at least locally caused phase-shifts of the x-ray radiation in the cardiac region by using a second grating for the passing-through x-ray radiation, designed as a phase grating, downstream of the patient in the emission direction;

measuring and reconstructing a spatial distribution of detected at least locally caused phase-shifts, wherein an average specific phase-shift value is assigned to each spatial unit;

assigning each of the at least two different tissue types to a region of a typical specific phase-shift value; and optically highlighting at least one region assigned to a tissue type in a view of the cardiac region.

2. The method as claimed in claim 1, wherein tissue types with different associated phase-shift value regions are optically highlighted in a different manner.

3. The method as claimed in claim 2, wherein the phase-shift value regions and their assignment to tissue types are stored in a look-up table.

4. The method as claimed in claim 2, wherein absorption data is also obtained in addition to the phase-contrast data.

5. The method as claimed in claim 1, wherein the phase-shift value regions and their assignment to tissue types are stored in a look-up table.

6. The method as claimed in claim 1, wherein absorption data is also obtained in addition to the phase-contrast data.

7. The method as claimed in claim 6, wherein at least one 3D absorption data record is reconstructed from the absorption data.

8. The method as claimed in claim 7, wherein a 3D view of the heart is generated from the at least one 3D absorption data record.

9. The method as claimed in claim 6, wherein the phase-contrast data is superposed on the 3D absorption view.

10. The method as claimed in claim 7, wherein the phase-contrast data is superposed on the 3D absorption view.

11. The method as claimed in claim 8, wherein the phase-contrast data is superposed on the 3D absorption view.

12. The method as claimed in claim 1, wherein cardiac phases of the scan of the patient are determined and wherein, in each case, measurement data of the same cardiac phases is processed together.

13. The method as claimed in claim 1, wherein at least the phase-contrast views are recorded using at least two temporally separated examinations, and wherein phase-contrast difference images of the temporally different phase-contrast views are generated.

14. The method as claimed in claim 13, wherein a 3D absorption data record is superposed on the phase-contrast difference images.

15. The method as claimed in claim 14, wherein absorption views are generated parallel to the phase-contrast views and the phase-contrast images are registered to the contours of the absorption images prior to the creation of phase-contrast difference images.

16. The method as claimed in claim 13, wherein absorption views are generated parallel to the phase-contrast views and the phase-contrast images are registered to the contours of the absorption images prior to the creation of phase-contrast difference images.

17. The method as claimed in claim 1, wherein at least one absorption view is generated after prior administration of an absorption contrast agent.

18. An x-ray computed tomography system, comprising:
at least one scanning system, to rotate about a system axis, including a radiation source, an x-ray absorption grating, a phase grating and a detector to determine at least one of absorption and phase-contrast, wherein a patient is placeable in a region between the x-ray absorption grating and the phase-contrast grating, and including a control and computational unit including a memory with computer programs to control the x-ray computed tomography system and to reconstruct tomographic views, the memory also including computer programs with program code, when executed in the control and computational unit, to carry out the method according to claim 1.

19. The method as claimed in claim 1, wherein the at least two different types of cardiac tissue include at least two of normally perfused tissue, hypoperfused tissue and scarred tissue.

20. A computer readable medium including program segments for, when executed on a computer device, causing the computer device to implement the method of claim 1.

21. An x-ray computed tomography system, comprising:
means for scanning at least one cardiac region of a patient by x-ray radiation which passes through a first grating for the passing-through x-ray radiation, designed as an absorption grating, prior to reaching the patient;

means for detecting at least locally caused phase-shifts of the x-ray radiation in the cardiac region by using a second grating for the passing-through x-ray radiation, designed as a phase grating, downstream of the patient in the emission direction;

means for measuring and reconstructing a spatial distribution of detected at least locally caused phase-shifts, wherein an average specific phase-shift value is assigned to each spatial unit;

means for assigning each of the at least two different tissue types to a region of a typical specific phase-shift value; and means for optically highlighting at least one region assigned to a tissue type in a view of the cardiac region.

* * * * *